United States Patent
Nambu et al.

[11] Patent Number: 5,883,158
[45] Date of Patent: Mar. 16, 1999

[54] PROCESS FOR PRODUCING IMPROVED SUPER ABSORBENT POLYMER

[75] Inventors: Hiromi Nambu; Akira Umada; Yoshihiko Watanabe; Tadashi Igarashi; Takayuki Amiya, all of Wakayama, Japan

[73] Assignee: Kao Corporation, Tokyo, Japan

[21] Appl. No.: 737,090

[22] PCT Filed: Aug. 10, 1995

[86] PCT No.: PCT/JP95/01602

§ 371 Date: Oct. 30, 1996

§ 102(e) Date: Oct. 30, 1996

[87] PCT Pub. No.: WO96/05234

PCT Pub. Date: Feb. 22, 1996

[30] Foreign Application Priority Data

Aug. 12, 1994 [JP] Japan .................................. 6-190342
Dec. 27, 1994 [JP] Japan .................................. 6-326127

[51] Int. Cl.$^6$ .............................. C08K 3/20; C08L 63/00
[52] U.S. Cl. ...................... 523/412; 523/408; 523/409; 524/500
[58] Field of Search .................... 523/409, 408, 523/412; 524/400

[56] References Cited

U.S. PATENT DOCUMENTS

| | | |
|---|---|---|
| 3,993,616 | 11/1976 | Gross . |
| 4,154,898 | 5/1979 | Burkholder, Jr. . |
| 4,727,097 | 2/1988 | Kobayashi et al. ............ 523/408 |
| 5,032,628 | 7/1991 | Choi et al. .................... 523/409 |
| 5,145,906 | 9/1992 | Chambers et al. ............ 524/732 |

FOREIGN PATENT DOCUMENTS

| | | |
|---|---|---|
| 50375 | 10/1981 | European Pat. Off. . |
| 163150 | 4/1985 | European Pat. Off. . |
| 233067 | 2/1987 | European Pat. Off. . |
| 341951 | 5/1989 | European Pat. Off. . |
| 347241 | 6/1989 | European Pat. Off. . |
| 481467 | 10/1991 | European Pat. Off. . |
| 521355 | 6/1992 | European Pat. Off. . |
| 605150 | 12/1993 | European Pat. Off. . |
| 3-429379 | 8/1984 | Germany . |
| 57-44627 | 3/1982 | Japan . |
| 58-117222 | 7/1983 | Japan . |
| 58-18690 | 5/1985 | Japan . |
| 61-211305 | 9/1986 | Japan . |
| 61-48521 | 10/1986 | Japan . |
| 61-264006 | 11/1986 | Japan . |
| 62-36411 | 2/1987 | Japan . |
| 63-99211 | 4/1988 | Japan . |
| 61-252212 | 3/1993 | Japan . |
| 6306118 | 11/1994 | Japan . |
| 2269602 | 2/1994 | United Kingdom . |

*Primary Examiner*—Melvyn I. Marquis
*Assistant Examiner*—D. Aylward
*Attorney, Agent, or Firm*—Birch, Stewart, Kolasch & Birch, LLP

[57] ABSTRACT

A process for producing an improved super absorbent polymer is disclosed. The process comprises adding to a water-retained super absorbent polymer retaining 10 to 100 parts by weight of water per 100 parts by weight of the super absorbent polymer, (a) a polyfunctional compound having two or more reactive groups and selected from a hydrophilic polymer or a metallic compound in an amount of 0.005 to 5 parts by weight per 100 parts by weight of the super absorbent polymer, and (b) a crosslinking agent having two or more functional groups capable of reacting with the polyfunctional compound at a weight ratio of the polyfunctional compound to the crosslinking agent of 0.1 to 30; mixing; and allowing the mixture to react by heating.

10 Claims, 1 Drawing Sheet

FIG.1
FIG.2
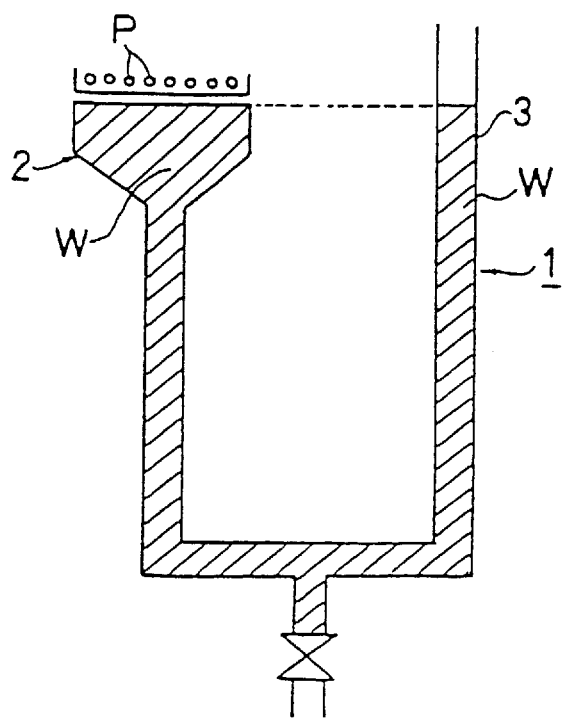
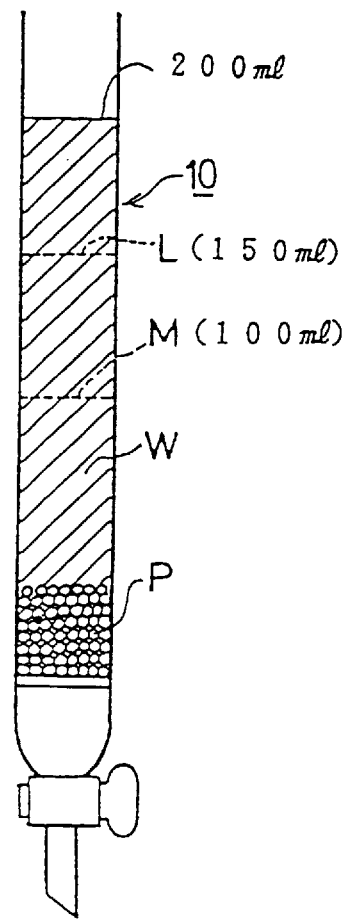

PROCESS FOR PRODUCING IMPROVED SUPER ABSORBENT POLYMER

FIELD OF THE INVENTION

This invention relates to a process for producing a super absorbent polymer. More particularly, it relates to a process for producing a super absorbent polymer which exhibits high water-absorbing properties, such as absorptivity, rate of absorption, and liquid permeability and, when swollen into a gel, exhibits excellent stability with time.

BACKGROUND OF THE INVENTION

While various types of super absorbent polymers have beer proposed to date and are known to the art from literature and patents, it is polyacrylic acid type super absorbent polymers that have been practically leading in the art. The term "polyacrylic acid type super absorbent polymer" as used herein denotes a polymer containing an acrylic acid monomer unit of at least 50 mol %, which is substantially water-insoluble but is highly swellable with water. Such polyacrylic acid type super absorbent polymers include polyacrylic acid crosslinked polymers or copolymers, starch-acrylonitrile grafted polymer hydrolyzates, starch-acrylic acid grafted crosslinked polymers, and vinyl acetate-acrylic ester copolymer saponified products. In these Polymers and copolymers 60 to 90 mol % of the carboxyl groups thereof generally have their hydrogen atom substituted with an alkali metal.

Super absorbent polymers are usually supplied for practical use in the form of powder or coating film. The performance of super absorbent polymers is evaluated in terms of absorptivity (absorption), rate of absorption, liquid Permeability, stability of swollen gel with time, and the like. Since many of these physical properties are conflicting with each other, it is very difficult to satisfy all these requirements, which has been a problem waiting for solution in further development of super absorbent polymers. For example, a super absorbent polymer having high absorptivity, i.e., a gel having a low degree of crosslinking, is inferior in rate of absorption, liquid permeability, and stability of swollen gel with time. On the other hand, a super absorbent polymer superior in rate of absorption, liquid permeability and stability of swollen gel with time, i.e., a gel having a high degree of crosslinking, tends to have low absorptivity.

In order to satisfy all the requirements, it has been proposed to improve practical performance by forming a highly crosslinked dense layer on the surface of a high absorbent polymer as disclosed in Japanese Patent Application Laid-opens 58-117222, 57-44627 and 63-99211, and Japanese Patent Publications 60-18690 and 61-48521. Japanese Patent Publication 5-19563, and Japanese Patent Application Laid-opens 61-211305, 61-264006 and 62-36411 disclose a method of graft treating a super absorbent polymer containing a carboxyl group and/or carboxylate group by using a silane coupling agent. Japanese Patent Application Laid-open 6-306118 proposes a method of treating with alkoxy titanium. Another known process comprises spraying an aqueous solution of a compound capable of readily reacting with the functional group, such as a carboxvlate group, of a super absorbent polymer, and then heating to form a highly crosslinked dense layer on a super absorbent polymer. Examples of the compound include a polyfunctional metal salt, a polyglycidyl ether and a polyisocyanate.

Another known process for producing a super absorbent polymer comprises adding to a super absorbent polymer a hydrophilic polymer having a reactive group and a crosslinking agent having at least two functional groups capable of reacting with the hydrophilic polymer and allowing the mixture to react by heating to coat the surface of the super absorbent polymer with the hydrophilic polymer with part of the functional group of the hydrophilic polymer being, crosslinked with the crosslinking agent. For example, Japanese Patent Application Laid-Open 60-36534 (corresponding to DE-A-3429379) discloses a process for producing a super absorbent polymer having a functional group on the surface thereof. According to this process, the aforesaid hydrophilic polymer is used in an amount as large as 1 to 30 parts by weight per 100 parts by weight of a super absorbent polymer to coat the surface of the super absorbent polymer, and a relatively small amount of a crosslinking agent is used to crosslink only a small portion of the hydrophilic polymer so that the functional group may remain effective. That is, the ratio of hydrophilic polymer to crosslinking agent is extremely high. For example, the ratio of the hydrophilic polymer to the crosslinking agent in the examples of JP-A 60-36534 is 40 to 180. This shows that the publication aims at employing a reactive group on the surface of a super absorbent polymer to change the quality of the super absorbent polymer, not at crosslinking the surface of the super absorbent polymer. Therefore, the process disclosed in the JP-A 60-36534 cannot provide a super absorbent polymer excellent in gel stability after swelling.

According to the process using a polyfunctional crosslinking agent capable of reacting with a carboxylate group, completion of the reaction requires a considerably long time, and strict conditions are imposed on adjustment of the water content of the super absorbent polymer at the time of crosslinking. In addition, it is necessary to moderately adjust not only the water content of the super absorbent polymer at the time of crosslinking but also the hydrophilic or hydrophobic properties and reactivity of the crosslinking agent in order to form a crosslinked layer in the vicinity of the surface layer of the super absorbent polymer, and it is extremely difficult to control the small thickness of the crosslinked layer. If the water content of the super absorbent polymer is reduced or if the crosslinking agent is rendered hydrophobic in order to form a thin crosslinked layer, the crosslinking efficiency of the crosslinking agent would be reduced or a desired crosslinking density could not be attained. Besides, a large proportion of the crosslinking agent, which is unfavorable for safety for use in sanitary materials, would remain in the final product.

DISCLOSURE OF THE INVENTION

An object of the present invention is to provide a process for producing a super absorbent polymer having high absorptivity while maintaining a satisfactory rate of absorption, liquid permeability, and stability of swollen gel with time.

In order to solve the above-mentioned problems, the inventors have conducted extensive investigations. As a result, it has been found that crosslinking for improving absorptivity of a super absorbent polymer can be achieved without reducing the rate of absorption, liquid permeability, and swollen gel stability with time by using a specific crosslinking agent in combination of a specific compound, and properly controlling the amounts of the compound to be crosslinked and the crosslinking agent.

The present invention has been reached based on the above finding. That is, the above object is accomplished by a process for producing an improved super absorbent polymer comprising adding to a water-retained super absorbent polymer retaining 10 to 100 parts by weight of water per 100 parts by weight of the super absorbent polymer, (a) a hydrophilic polymer having two or more reactive groups selected from an amide group, a hydroxyl group, an amino group, an aldehyde group, a sulfo group and a carboxyl group, or a metallic compound of silicon, titanium or zirconium having two or more reactive groups selected from an alkoxyl group, a halogen group, an isocyanate group and an acyloxy group, in an amount of 0.005 to 5 parts by weight per 100 parts by weight of the super absorbent polymer, and (b) a crosslinking agent capable of reacting with the hydrophilic polymer or the metallic compound, provided that:

the crosslinking agent for the hydrophilic polymer is at least one member selected from the group consisting of a polyglycidyl ether, a haloepoxy compound, a polyaldehyde, a polyol and a polyamine, and the crosslinking agent for the metallic compound has two or more functional groups selected from a hydroxyl group, an epoxy group, a carboxyl group, an amino group and a thio group, at a weight ratio of the hydrophilic polymer or the metallic compound to the crosslinking agent of 0.1 to 30; mixing; and allowing the mixture to react by heating.

In the improved super absorbent polymer obtainable by the process of the present invention, a crosslinked layer is formed on or in the vicinity of the surface of the improved super absorbent polymer, and the crosslinked layer exhibits improved stability with time when the improved super absorbent polymer is swollen into a gel.

BRIEF DESCRIPTION OF THE DRAWINGS

FIG. 1 is a schematic illustration showing the apparatus for measuring a rate of water absorption, used in Examples and Comparative Examples; and FIG. 2 is a schematic illustration showing the apparatus for measuring the rate of permeation to physiological saline, used in Examples and Comparative Examples.

BEST MODE FOR CARRYING OUT THE INVENTION

The super absorbent polymer which can be used in the process of the present invention preferably has a water absorptivity of about 10 to 1500 times its own weight. In particular, a preferred example of the super absorbent polymer is hydrophilic polymers having a carboxyl group and/or a carboxylate group in the constituent unit thereof. However, it is not limited thereto and no restriction is imposed on the kind of the super absorbent polymer or the method of polymerization. Illustrative examples of super absorbent polymers which are suitable for use in the present invention include poly(sodium acrylate) prepared by reverse phase suspension polymerization, which is described in Japanese Publication 54-30710, Japanese Patent Application Laid-opens 51-120591, 56-26909, 6-93008 and 6-136012, and International Publication WO94/20543 which are incorporated herein by reference; poly(sodium acrylate) prepared by aqueous solution polymerization (adiabatic polymerization or thin film polymerization) described in Japanese Patent Application Laid-Open 55-133413 which is incorporated herein by reference; and (starch-sodium acrylate) graft polymers described in Japanese Patent Publication No. 53-46199 which is incorporated herein by reference.

Super absorbent polymers having a carboxyl group and/or a carboxylate group in the constituent unit thereof are generally polymers or copolymers of acrylic acid or an alkali metal salt thereof, or polymers or copolymers of methacrylic acid or an alkali metal salt thereof, such as polyacrylic acid or salts thereof and polymethacrylic acid and salts thereof. These super absorbent polymers can be preferably used for the process according to the present invention. The salts of polyacrylic acid or polymethacrylic acid preferably include sodium salts. Copolymers obtainable by copolymerizing acrylic acid or methacrylic acid and a comonomer such as maleic acid, itaconic acid, acrylamide, 2-acrylamido-2-methylpropanesulfonic acid, 2-(meth)acryloylethanesulfonic acid, 2-hydroxyethyl (meth)acrylate and styrenesulfonic acid, which are copolymerized at such a ratio that the comonomers do not impair the performance of the super absorbent polymer, can also be used for preference in the present invention. When a polymer of acrylic acid is neutralized to obtain its salt, a preferred degree of neutralization is 30 to 90 mol %, still preferably 60 to 90 mol % in view of absorption property and production cost. When producing the polymers, if desired, a compound for crosslinking the polymers can be used as far as the performance of the super absorbent polymer is not impaired.

Examples of the compound for crosslinking the polymers include divinyl compounds such as N,N'-methylene-bis-acrylamide and (poly)ethyleneglycol di-(meth)acrylate; diglycidyl ethers such as (poly)ethyleneglycol diglycidyl ether; a halo-epoxy compounds such as epichrolehidrin; polyaldehydes such as glutaraldehyde and glyoxal; polyols such as ethylene glycol and glycerin; and polyamines such as ethylene-diamine.

Particularly preferred super absorbent polymers are those obtainable by reverse phase (W/O) suspension polymerization. In the present invention, water is added to a super absorbent polymer to prepare a water-retained super absorbent polymer. In this case, a super absorbent polymer should be dehydrated after synthesis. In this connection, polymers obtainable by reverse phase suspension polymerization are advantageous for workability.

Where reverse phase suspension polymerization is adopted for the preparation of a super absorbent polymer, a conventional method described in the literature cited above may be followed, in which a water-soluble initiator such as a persulfate, 2,2'-azobis (2-amidinopropane) dihydrochloride, is added to an aqueous solution of a hydrophilic monomer having a carboxyl group and/or a carboxylate group and then the system is subjected to reverse phase suspension polymerization by using a dispersing agent for use in reverse phase suspension polymerization and/or a protective colloid.

Examples of the protective colloids include sorbitan fatty acid esters such as sorbitan monostearate, sorbitan monolaurate and polyoxyethylene sorbitan monooleate; cationic and amphoteric surface active agents such as trimethyl stearyl ammonium chloride and carboxymethyldimethyl-cetylammonium; anionic surface active agents such as sodium polyoxyethylene dodecyl ether sulfate and sodium dodecyl ether sulfate ester; glycoside compounds such as an alkyl glycoside and gluconamide; cellulose ethers such as ethyl cellulose and benzyl cellulose; cellulose esters such as cellulose acetate, cellulose butyrate and cellulose acetate butyrate; and polymeric dispersants such as maleic acid modified polybutadiene, maleic acid modified polyethylene, maleic acid modified α-olefins, a styrene-dimethylaminoethyl methacrylate quaternary salt and an isopropyl methacrylate-dimethylaminoethyl methacrylate quaternary salt. These compounds may be used either individually or as a combination of two or more thereof.

Non-aqueous solvents to be used in reverse phase suspension polymerization include aliphatic hydrocarbons such as hexane, heptane and octane; alicyclic hydrocarbons such as cyclohexane, methylcyclohexane and decalin; and halogenated hydrocarbons such as chlorobenzene, bromobenzene and dichlorobenzene.

The super absorbent polymer to be used is not particularly limited in shape and may be spherical, flaky or irregular. The super absorbent polymer particles preferably have a particle size of 50 to 2000 $\mu$m, still preferably 100 to 1000 $\mu$m, from the standpoint of ease in handling.

In the present invention, 10 to 100 parts by weight, preferably 20 to 50 parts by weight, of water is added to 100 parts by weight of a dried super absorbent polymer to obtain a water-retained super absorbent polymer. If the water content is less than 10 parts by weight, a crosslinked structure comprising the polyfunctional compound and the crosslinked agent cannot be formed on the surface of the super absorbent polymer. If the water content exceeds 100 parts by weight, not only is reduced the absorption of the resulting super absorbent polymer but also the crosslinked structure is formed in the inside of the super absorbent polymer, not in the vicinity of the surface of the super absorbent polymer, or the particles of the super absorbent polymers tend to stick together, so that the particles cannot be obtained reliably.

According to the process of the present invention, to the thus prepared water-retained super absorbent polymer are added prescribed amounts of (a) a polyfunctional compound having two or more reactive groups and selected from a hydrophilic polymer or a metallic compound of silicon, titanium or zirconium, and (b) a crosslinking agent having two or more functional groups capable of reacting with the polyfunctional compound. The polyfunctional compound (a) and the crosslinking agent (b) may be added at the same time, or addition of the polyfunctional compound (a) may be followed by addition of the crosslinking agent (b). The latter mode of addition is preferred for crosslinking efficiency.

The polyfunctional compound having two or more reactive groups (a) will be described in detail. The polyfunctional compound is, as described above, selected from a hydrophilic polymer or a metallic compound of silicon, titanium or zirconium.

Where the hydrophilic polymer having two or more reactive groups is used as the polyfunctional compound (a), any hydrophilic polymer can be used with no restriction so far as the hydrophilic polymer has reactive groups capable of chemically reacting with functional groups of the crosslinking agent and has hydrophilicity.

Reactive groups of the hydrophilic polymer include, for example, an amide group, a hydroxyl group, an amino group, an aldehyde group a sulfo group, and a carboxyl group, with an amide group, a hydroxyl group and an amino group being preferred. These reactive groups in the hydrophilic polymer may be the same or different.

Examples of hydrophilic polymers having such reactive groups include polymers and copolymers of a nitrogen-containing vinyl monomer such as (meth)acrylamide, N,N-dimethylaminoethyl (meth)acrylate, N,N-dimethylaminoethyl (meth)acrylate and a methyl chloride-quaternarized compound thereof, N,N-diethylaminoethyl (meth)acrylate and a methyl chloride-quaternarized compound thereof, vinylpyridine, vinylpyrrolidone and allylamine; polymers and copolymers of a hydroxyl-containing vinyl monomer such as poly[2-hydroxyethyl (meth)acrylate], polyethylene glycol (meth)acrylate and polyvinyl alcohol; polymers and copolymers of a sulfo-containing vinyl monomer such as vinylsulfonic acid, styrenesulfonic acid and 2-acrylamido-2-methylpropanesulfonic acid; polyethyleneimine; polyacrolein; polyethylene glycol; and a Hofmann degradation product of polyacrylamide. In particular, polymers and copolymers of a nitrogen-containing vinyl monomer and polyethyleneimine are preferably used, with polyethyleneimine being the most preferred. The hydrophilic polymers may be used either individually or as a combination of two or more thereof.

While not limiting, the molecular weight of the hydrophilic polymer to be used preferably ranges from 500 to 500,000.

Where a metallic compound of silicon, titanium or zirconium having two or more reactive functional groups is used as the polyfunctional compound (a), any metallic compound of silicon, titanium or zirconium can be used so far as the metallic compound has the reactive groups capable of chemically reacting with the functional groups of the crosslinking agent.

It is still preferred that a hydrolyzable groups are used as the reactive groups. The "hydrolyzable group" as used herein means a group which can react with water to convert into a hydroxyl group so as to provide a metal hydroxide.

Examples of the hydrolyzable group include, for example, alkoxy group (preferably having 1 to 5 carbon atoms), halogen group such as chloride, an isocyanate group and an acyloxy group (preferably alkanoyloxy group having 2 to 4 carbon atoms), while not limited thereto. Preferred of them is alkoxy group, with ethoxy group being still preferred. The hydrolyzable groups in the metallic compound may be the same or different.

The above-mentioned metals include IVA group metals such as silicon, IVB group metals such as titanium and zirconium, with silicon and titanium being still preferred. The above-mentioned metallic compounds can be used either individually or as a combination of two or more thereof.

Examples of the above-mentioned metallic compound using silicon as the metal include alkoxy silanes such as tetraethoxysilane, methyltriethoxysilane, diphenyldiethoxysilane and tetraethoxysilane polymer; chlorosilanes such as tetrachlorosilane and dimethyldichlorosilane; silane coupling agents such as 3-aminopropyltriethoxysilane, 3-methacryloxypropyl-trimethoxysilane, 3-glycidoxypropyl-trimethoxysilane, 3-mercaptopropyl-triethoxysilane, 3-chloropropyl-methyl-dimethoxysilane, vinyltrichlorosilane, vinyltriethoxysilane and vinyltriacetoxysilane; and silylisocyanate such as dimethylsilyldiisocyanate, ethoxysilanediisocyanate and vinylsilyltriisocyanate. Preferred among them are alkoxysilane, with tetraethoxysilane and polymers thereof being still preferred.

Examples of the above-mentioned metallic compounds using titanium include tetraisopropoxytitanium, and the dimers and polymers thereof; tetrabutoxytitanium, and the dimers and polymers thereof; alkoxytitanium, such as diisopropoxybis(acetylacetonato)titanium, dibutoxybis(triethanolaminato)titanium, tetraisopropylbis(dioctylphosphite)titanate; organic titanate including titaniumacylate such as tetrastearoxytitanium and dihydroxybis (lactato)-titanium. Preferred among them is alkoxytitanium, with diisopropoxybis(acetylacetonato)titanium and dibutoxybis(triethanolaminato)titanium being still preferred.

Examples of the metallic compounds using zirconium as the metal include tetraisopropylzirconate, tetrabutylzirconate and zirconium acetylacetonate. Zircoaluminate coupling agents can be also used. Preferred among them are tetraisopropylzirconate and tetrabutylzirconate.

Still preferred among the above-mentioned metallic compounds are alkoxy silane and alkoxy titanium in view of performance, cost, ease in handling and safety of the improved super absorbent polymer to be obtained.

The amount of the polyfunctional compound to be added to the super absorbent polymer can be varied widely according to the end use. It usually ranges from 0.005 to 5 parts by weight, preferably 0.01 to 1 part by weight, still preferably 0.05 to 0.8 part by weight, per 100 parts by weight of the super absorbent polymer. If the amount of the polyfunctional compound is less than 0.005 part, the crosslinked structure is not formed sufficiently on the surface of the super absorbent polymer, thereby failing to exhibit advantageous effects. Even if the amount of the polyfunctional compound exceeds 5 parts, no further improvement in physical properties of the improved super absorbent polymer to be obtained is achieved. Further, too strong crosslinked structure may sometimes incur reductions in absorption and rate of absorption of the improved super absorbent polymer.

The crosslinking agent (b) will be described in detail. The crosslinking agent has two or more functional groups capable of reacting with the polyfunctional compound. Any functional groups can be used as far as the functional groups can react with the reactive groups of the polyfunctional compound, or the functional groups can convert into functional groups that can react with the reactive groups of the polyfunctional compounds.

As will be described later, in the present invention, the degree of crosslinking, that is, weight ratio of the polyfunctional compound to the crosslinking agent is of great importance. Specifically, if the degree of crosslinking is too low, the crosslinked structure become fragile, so that the stability of the swollen gel is reduced with time. If the degree of crosslinking is too high, the surface of the super absorbent polymer is firmly covered with the crosslinked structure, so that absorbency is reduced.

Where the hydrophilic polymers are used as the polyfunctional compound (a), not limiting examples of the functional groups of the crosslinking agent include a glycidyl group, an aldehyde group and an isocyanate group, with a glycidyl group being preferred.

Where the metallic compounds of silicon, titanium or zirconium are used as the polyfunctional compound (a), not limiting examples of the functional groups include a hydroxyl group, a carboxyl group, an amino group and a thio group, with a hydroxyl group being preferred. Not limiting examples of the group which can be converted into a functional group capable of reacting with the reactive group of the polyfunctional compound include an epoxy group, an ester group and an amide group, with an epoxy group being preferred.

The functional groups in the crosslinking agent are may be the same or different. The crosslinking agent may have both the functional group and the group which can be converted into the functional group.

Where the hydrophilic polymer is used as the polyfunctional compound (a), the crosslinking agent is preferably at least one compound selected from the group consisting of a polyglycidyl ether, a halo-epoxy compound, a polyaldehyde, a polyol, and a polyamine. More specifically, examples of the polyglycidyl ethers include ethylene glycol diglycidyl ether (EGDG), polyethylene glycol diglycidyl ether and polyglycerol polyglycidyl ether (PGPG). Examples of the halo-epoxy compounds include epichlorohydrin (ECH) and α-methylchlorohydrin. Examples of the polyaldehydes include glutalaldehyde and glyoxal. Examples of the polyols include glycerin, pentaerythritol and ethylene glycol. Examples of the polyamines include ethylenediamine. These crosslinking agents may be used either individually or as a combination of two or more thereof.

Where the metallic compound of silicon, titanium or zirconium is used as the polyfunctional compound (a), examples of the crosslinking agent include polyols such as ethylenegylcol, glycerin, pentaerythritol, polyglycerin, polyvinylalcohol, hyroxyethylcellulose and poly(2-hyroxyethyl(meth)acrylate); polyglycidylethers such as EGDG, (poly)ethyleneglycolpolyglycidylether, PGPG and sorbitolpolyglycidylether; polycarboxylic acids such as succinic acid, citric acid, tartaric acid, and poly(meth)acrylic acid; polyamines such as ethylenediamine, polyethylene imine and polyallyamine; and polyols such as 1,2-dimercaptoethane. Preferred among them are polyols and polyglycidyl ethers in view of the performance, color and scent of the improved super absorbent polymer to be obtained. These crosslinking agents may be used either individually or as a combination of two or more of them.

Preferred among the above-mentioned polyols are glycerin, polyglycerin and polyvinyl alcohol, with polyglycerin being still preferred.

Preferred among the polyglycidyl ethers are (poly)ethyleneglycolpolyglycidyl ether and PGPG, with PGPG being still preferred.

A particularly preferred combination of the above-mentioned metallic compound and the above-mentioned crosslinking agent is a combination of alkoxy titanium or alkoxy silane (metallic compound), and polyol and/or polyglycidyl ether (crosslinking agent).

The amount of the crosslinking agent to be added is preferably from 0.005 to 10 parts by weight, more preferably from 0.005 to 1 part by weight, per 100 parts by weight of the super absorbent polymer, while varying depending on the kind of the crosslinking agent.

As previously mentioned, the weight ratio of the polyfunctional compound to the crosslinking agent is of great importance in the present invention. While varying depending on the kind of the polyfunctional compound and the crosslinking agent to be used, and on the water content of the water-retained super absorbent polymer, the weight ratio of the polyfunctional compound to the crosslinking agent ranges usually from 0.1 to 30, preferably from 0.1 to 20, more preferably from 0.1 to 10, still preferably from 0.5 to 10. If the weight ratio exceeds 30, the degree of crosslinking is insufficient for sufficiently forming a network structure of the polyfunctional compound, failing to provide the improved super absorbent polymer excellent in swollen gel stability with time. If the weight ratio is less than 0.1, the polyfunctional compound undergoes excessive crosslinking to reduce the water-absorbing function of the improved super absorbent polymer.

The polyfunctional compound and the crosslinking agent may be added to the water-retained super absorbent polymer at the same time. In view of crosslinking efficiency, however, it is preferred that the polyfunctional compound is first added to water-retained super absorbent polymer to cover the surface of the water-retained super absorbent polymer, followed by addition of the crosslinking agent.

Addition of the polyfunctional compound and the crosslinking agent to the water-retained super absorbent polymer may be conducted while keeping them as they are, or alternatively after dissolving them in a suitable solvent. In particular, where the metallic compound of silicon, titanium or zirconium having the hydrolyzable groups is added as the polyfunctional compound, the hydrolyzable group may be previously hydrolyzed under an appropriate condition and then added to the suspension of the water-retained super absorbent polymer.

A method of adding the polyfunctional compound and the crosslinking agent will be described in more detail. For example, in using a super absorbent polymer obtainable by reverse phase suspension polymerization, a water-retained super absorbent polymer having a water content controlled within the above-described range is suspended in an organic solvent, and the above-described polyfunctional compound is added thereto. If desired, a dispersant for reverse phase suspension polymerization, such as ethyl cellulose, a sugar ester and a sorbitan ester, may be optionally added to the system either before or after the addition of the polyfunctional compound. Thereafter, the above-mentioned crosslinking agent is added thereto, followed by heating the system to react. The heating temperature is usually from 50° to 100° C. Alternatively, the polyfunctional compound is previously dispersed in a non-polar solvent in the presence of a dispersant, and the resulting dispersion is added to a suspension of the super absorbent polymer having a controlled water content.

In the case of using a water-retained super absorbent polymer prepared from a super absorbent polymer obtainable by other polymerization methods, such as aqueous solution polymerization, or a commercially available super absorbent polymer, coating with the polyfunctional compound can be carried out as follows. In using a super absorbent polymer obtainable by aqueous solution polymerization, the super absorbent polymer gel obtained is broken into pieces, and the water content is adjusted to the above-recited range by, for example, drying. The thus prepared water-retained super absorbent polymer is charged into a kneader, and, if desired, a dispersant such as ethyl cellulose, a sugar ester and a sorbitan ester, or one or more of the surface active agents selected from an anionic surface active agent, a cationic surface active agent and a nonionic surface active agent is/are added thereto. If desired, a polar or non-polar organic solvent may also be added as a dispersing medium. Then, the above-mentioned polyfunctional compound is added thereto, and the above-mentioned crosslinking agent is added, followed by heating. Heating is desirable for smooth progress of surface coating. The crosslinking agent is preferably reacted at a temperature ranging from 40° to 150° C.

The organic solvent referred to above as a dispersing medium is not particularly limited, but those having a boiling point between 30° and 200° C. are recommended in view of safety as well as workability. Preferred polar solvents include, for example, methanol, ethanol, isopropyl alcohol, chloroform and toluene, and preferred examples of the non-polar solvents include, for example, aliphatic hydrocarbons and alicyclic hydrocarbons such as n-hexane, cyclohexane, and ligroin.

Another illustrative method of adding the polyfunctional compound and the crosslinking agent is a method in which a kneader is used without using dispersant.

In order to form the uniform crosslinked structure comprising the polyfunctional compound and the crosslinking agent on the surface of the water-retained super absorbent polymer, most preferred among the above-mentioned various methods is the method in which a dispersant is used. In particular, in view of processability, it is preferred that the super absorbent polymer is polymerized by reverse phase suspension polymerization, followed by adjusting water content in the super absorbent polymer, and then the polyfunctional compound and the crosslinking agent are added to the system, forming a crosslinked structure on the surface of the super absorbent polymer.

It is considered that the improved super absorbent polymer obtainable by the process of the present invention has a crosslinked network structure comprising the polyfunctional compound and the crosslinking agent on or in the vicinities of the surface of the super absorbent polymer so that the improved super absorbent polymer exhibits not only high water absorptivity but excellent swollen gel stability with time.

Further, the improved super absorbent polymer obtainable by the process of the present invention can be changed its form into a single absorbent material in which the polymer particles are fixed. For instance, in preparing polyurethane from an organic polyisocyanate and a polyol, the super absorbent polymer having its surface coated with partially crosslinked polyethyleneimine can be added to the reaction system to provide an absorbent material having a continuous structure in which the super absorbent polymer is covalently bonded. Such an absorbent material is expected to be widely applicable as sanitary materials, water-retaining materials, water-stopping materials, dehydrating materials, materials for preventing dew drop condensation which are incorporated into plastic building materials, and packaging materials which are blended with other polymers.

Besides the conventional uses in the sanitary field and agricultural field, the improved super absorbent polymer obtainable by the process of the present invention will find new uses as polymeric catalysts represented by phase transfer catalysts or oxygen-fixed supports, chelating polymers capable of capturing heavy metals, noble metals or harmful metals, coagulating polymers, or ion-exchange polymers.

EXAMPLES

The present invention will now be illustrated in greater detail with reference to Examples and Comparative Examples, but it should be understood that the present invention is not construed as being limited thereto.

Methods of testing conducted in Examples and Comparative Examples are as follows.
Measurement of Absorption:

One gram of a super absorbent polymer was dispersed in great excess of physiological saline (0.9% aqueous solution of sodium chloride) and allowed to be swollen to equilibrium. The physiological saline was removed by filtration through an 80 mesh metal net, and the weight (W) of the water-retained super absorbent polymer was measured. A quotient obtained by dividing the value W by the weight of the super absorbent polymer before absorption ($W_0$), i.e., $W/W_0$, was taken as an absorption (g/g).
Measurement of Rate of Absorption:

Demand wettability tester 1 shown in FIG. 1 which is commonly known as an apparatus for carrying out a DW (demand wettability) method is used. As shown in FIG. 1, physiological saline W is put in the tester with the two liquid levels being equal, and 0.3 g of super absorbent polymer P is scattered on mounting 2 (diameter: 70 mm; No. 1 glass filter carrying thereon No. 2 filter paper). Taking the water absorption at the time of scattering the super absorbent polymer as zero, the absorption after 3 minutes is measured by reading the scale on the burette 3 indicating a drop of the liquid level of physiological saline W. The measured value is taken as an absorption (ml) representing the rate of absorption.

Measurement of Rate of Liquid Permeation:

In apparatus 10 shown in FIG. 2 (a burette comprising a glass cylinder having an inner diameter of 25.6 mm and a length of about 500 mm) is put 0.5 g of a super absorbent polymer and swollen to equilibrium with excess physiological saline. The cock is closed with the liquid level adjusted to a height of 200 ml from the bottom. On confirming that the swollen super absorbent polymer P has been sedimented sufficiently as illustrated, the cock is opened, and the time required for physiological saline W to pass through the section between two gage marks, L (150 ml high from the bottom) and M (100 ml high from the bottom), which corresponds to a 50 ml portion, is measured. The amount (ml) of the liquid between the gage marks is divided by the measured time (min) to obtain a rate of liquid permeation (ml/min).

Evaluation of Swollen Gel Stability with Time:

One gram of a super absorbent polymer is swollen with 45 g of physiological saline containing 0.05% L-ascorbic acid, sealed into a screw tube, and allowed to stand at 40° C. for 3 hours. The state of the swollen gel is observed to evaluate stability with time.

The swollen gel stability with time is rated in fluidity, stringiness, and shape retention according to a 4-grade system shown in Table 1 below. Samples rated "Good" or higher are suitable as a water-absorbing polymer for use in sanitary napkins, disposable diapers, shirts for adults, tampons, absorbent wadding, etc.

TABLE 1

| Evaluation | Fluidity | Stringiness | Shape Retention |
|---|---|---|---|
| Excellent | not observed | not observed | no change |
| Good | slightly observed | slightly observed | slightly changed |
| Fair | observed | observed | partially liquefied |
| Poor | observed | observed | more than half was liquefied |

Example 1

In a 1000 ml-volume 4-necked flask equipped with a stirrer, a reflux condenser, a dropping funnel, and a tube for introducing nitrogen gas were charged 400 ml of cyclohexane and 0.625 g of ethyl cellulose (Ethyl Cellulose N-100, produced by Hercules), and nitrogen gas was blown into the mixture to purge dissolved oxygen. The mixture was heated up to 75° C. Separately, 102.0 g of acrylic acid in a separate flask was diluted with 25.5 g of ion-exchanged water and neutralized by addition of 140 g of a 30 wt % aqueous solution of sodium hydroxide while externally cooling. A solution of 0.204 g of potassium persulfate in 7.5 g of water was added thereto and dissolved, and nitrogen gas was bubbled through the solution to remove any oxygen remaining in the solution. The contents of the flask were added dropwise to the aforementioned 4-necked flask over a period of 1 hour to conduct polymerization. After completion of the polymerization, the reaction mixture was azeotropically dehydrated by means of a drying tube to adjust the water content of the super absorbent polymer to 30 parts by weight per 100 parts by weight of the polymer. To the thus prepared water-retained super absorbent polymer dispersed in cyclohexane was added a solution of 0.255 g (0.25 wt % based on the acrylic acid) of polyethyleneimine (Epomine SP-006, produced by Nippon Shokubai) in 5 g of water, followed by stirring at 75° to 80° C. for 15 minutes to form a coating layer of polyethyleneimine on the surface of the water-retained super absorbent polymer. Then, a solution of 0.102 g (0.10 wt % based on the acrylic acid) of polyglycerol polyglycidyl ether (Denacol EX-512, produced by Nagase Kasei) in 4 g of water was added thereto, followed by reacting at 75° to 80° C. for 1 hour to crosslink the polyethyleneimine. The resulting gel was collected and dried under reduced pressure to obtain sodium polyacrylate having a crosslinked polyethyleneimine coating layer on the surface thereof. The improved super absorbent polymer thus obtained was evaluated in terms of absorption, rate of absorption, rate of liquid permeation and swollen gel stability with time using physiological saline, and the results obtained are shown in Table 2 below.

Example 2 To 17

Improved super absorbent polymers were obtained in the same manner as in Example 1, except for changing the kinds and amounts of the hydrophilic polymer, crosslinking agent, and dispersant for reverse phase suspension polymerization as shown in Table 2. The resulting super absorbent polymers were evaluated by the same manner as in Example 1. The results obtained are shown in Table 2.

TABLE 2

| Examples | Hydrophilic Polymer Type/MW/wt %*) | Crosslinking Agent Type/wt %*) | Hydrophilic Polymer/ Crosslinking Agent (wt/wt) | Water Content | Dispersant Type/wt %*) | Absorption g/g | Rate of Absorption ml/0.3 g | Rate of Liquid Permeation ml/min | Stability |
|---|---|---|---|---|---|---|---|---|---|
| 1 | PEI/600/0.25 | PGPG/0.10 | 2.5 | 30 | EC/0.5 | 64.2 | 6.3 | 38.5 | Good |
| 2 | PEI/600/0.10 | EGDG/0.05 | 2.0 | 30 | EC/0.5 | 64.8 | 6.5 | 39.2 | Good |
| 3 | PEI/1,800/0.25 | PGPG/0.10 | 2.5 | 30 | SuE/2.0 | 62.1 | 6.1 | 54.5 | Good |
| 4 | PEI/1,800/0.50 | PGPG/0.10 | 5.0 | 30 | SoE/3.0 | 66.6 | 6.2 | 27.3 | Good |
| 5 | PEI/10,000/0.25 | PGPG/0.15 | 1.67 | 25 | EC/0.5 | 63.2 | 6.5 | 44.8 | Good |
| 6 | PEI/70,000/0.25 | PGPG/0.10 | 2.5 | 30 | EC/0.5 | 69.1 | 7.0 | 30.1 | Good |
| 7 | PEI/70,000/0.25 | PGPG/0.15 | 1.67 | 35 | EC/0.5 | 60.4 | 5.8 | 55.6 | Excellent |
| 8 | PEI/70,000/0.80 | EGDG/0.10 | 8.0 | 50 | EC/0.5 | 55.3 | 5.9 | 68.0 | Excellent |
| 9 | PEI/600/0.25 | PGPG/0.15 | 1.67 | 30 | EC/0.5 | 60.0 | 10.1 | 114.3 | Good |
| 10 | PEI/70,000/0.25 | PGPG/0.15 | 1.67 | 35 | AG/1.0 | 58.2 | 8.5 | 152.2 | Good |

TABLE 2-continued

| Examples | Hydrophilic Polymer Type/MW/wt %*) | Crosslinking Agent Type/wt %*) | Hydrophilic Polymer/ Crosslinking Agent (wt/wt) | Water Content | Dispersant Type/wt %*) | Absorption g/g | Rate of Absorption ml/0.3 g | Rate of Liquid Permeation ml/min | Stability |
|---|---|---|---|---|---|---|---|---|---|
| 11 | PVA/20,000/0.35 | PGPG/0.10 | 3.5 | 30 | EC/0.5 | 59.8 | 6.1 | 53.9 | Good |
| 12 | PAlAm/10,000/0.15 | PGPG/0.10 | 1.5 | 10 | EC/0.5 | 55.2 | 5.7 | 62.3 | Good |
| 13 | PEAm/3,000/0.25 | ECH/0.30 | 0.83 | 30 | EC/0.5 | 58.6 | 5.7 | 48.8 | Good |
| 14 | PQDM/100,000/0.25 | PGPG/0.10 | 2.5 | 25 | EC/0.5 | 62.4 | 6.3 | 38.0 | Good |
| 15 | PHEA/10,000/0.30 | PGPG/0.20 | 1.5 | 30 | EC/0.5 | 57.8 | 6.4 | 51.7 | Good |
| 16 | PTEGA/10,000/0.50 | ECH/0.10 | 5.0 | 35 | EC/0.5 | 52.7 | 5.9 | 65.4 | Excellent |
| 17 | PDMAEA/8,000/0.20 | PGPG/0.25 | 0.8 | 40 | EC/0.5 | 51.7 | 5.9 | 58.5 | Excellent |

*)Based on produced polymer
Note:
1) Hydrophilic Polymers
PEI: polyethyleneimine produced by Nippon Shokubai
Epomine SP-006 (MW = 600)
Epomine SP-018 (MW = 1800)
Epomine SP-200 (MW = 10,000)
Epomine P-1000 (MW = 70,000; supplied in the form of a 30 wt % aqueous solution; the amount shown in Table 2 corresponds to only the polymerous content)
PVA: polyvinyl alcohol (degree of polymerization: 500), produced by Wako Pure Chemical Industries, Ltd.
PAlAm: polyallylamine PAA-L (MW = 10,000), produced by Nitto Boseki Co., Ltd.
PEAm: ethylene oxide adduct of ethylenediamine Pluronic TR704 (MW = 5,000), produced by Asahi Denka Kogyo K.K.
PQDM: polydimethylaminoethyl methacrylate quaternarized with methyl chloride (MW = 100,000)
PHEA: polyhydroxyethyl acrylate (MW = 70,000)
PTEGA: polytetraethylene glycol acrylate (MW = 150,000)
PDMAEMA: polydimethylaminoethyl methacrylate (MW = 100,000)
2) Crosslinking Agents
EGDG: ethylene glycol diglycidyl ether Denacol EX-10, produced by Nagase Kasei
PGPG: polyglycerol polyglycidyl ether Denacol EX-512, produced by Nagase Kasei
ECH: epichlorohydrin, produced by Wako Pure Chemical
3) Water Content
Parts by weight per 100 parts by weight of the dried super absorbent polymer
4) Dispersant
EC: Ethyl Cellulose N-100, produced by Hercules
SuE: Ryoto Sugar Ester S-570, produced by Mitsubishi Kasei Shokuhin K.K.
SoE: sorbitan ester Leodor SP-S10, produced by Kao Corporation
ES: polyoxyethylene alkyl ether sulfate Emal E-27C, produced by Kao Corporation
AG: dodecyl glucoside (degree of sugar condensation: 1.25)

Example 18

In a 1000 ml-volume 4-necked flask equipped with a stirrer, a reflux condenser, and a dropping funnel were charged 125 g of Aquaric CAW-4 (aqueous solution polymerization type super absorbent polymer, produced by Nippon Shokubai) having been dried at 120° C. and 0.5 mmHg for 24 hours, 400 ml of cyclohexane, and 0.625 g of ethyl cellulose (Ethyl Cellulose N-100, produced by Hercules), and the mixture was heated to 75° to 80° C. After heating, 37.5 g of ion-exchanged water was added thereto, followed by stirring under reflux for 30 minutes thereby to adjust the water content of the super absorbent polymer at 30 parts by weight per 100 parts by weight of the super absorbent polymer. To the thus prepared water-retained super absorbent polymer dispersed in cyclohexane was added a solution of 0.25 g (0.20 wt % based on the super absorbent polymer) of polyethyleneimine (Epomine SP-006, produced by Nippon Shokubai) in 5 g of water, followed by stirring at 75° to 80° C. for 15 minutes to form a coating layer of polyethyleneimine on the surface of the super absorbent polymer. Then, a solution of 0.102 g (0.10 wt % based on the super absorbent polymer) of polyglycerol polyglycidyl ether (Denacol EX-512, produced by Nagase Kasei) in 4 g of water was added thereto, followed by reacting at 75° to 80° C. for 1 hour to crosslink the polyethyleneimine. The resulting gel was collected and dried under reduced pressure to obtain an improved super absorbent polymer having a crosslinked polyethyleneimine coating layer on the surface thereof. The resulting super absorbent polymer was evaluated by the same manner as in Example 1, and the results obtained are shown in Table 3.

Example 19

An improved super absorbent polymer was prepared by conducting crosslinking treatment in the same manner as in Example 18, except for replacing super absorbent polymer Aquaric CAW-4 of Example 18 with Diawet USII-60 (suspension polymerization type super absorbent polymer, produced by Mitsubishi Petrochemical Co., Ltd., using the kinds and amounts of the hydrophilic polymer, crosslinking agent and dispersant as shown in Table 3, and adding the hydrophilic polymer at the water content shown in Table 3. The resulting super absorbent polymer was evaluated by the same manner as in Example 1. The results obtained are shown in Table 3.

Example 20

An improved super absorbent polymer was prepared by crosslinking treatment in the same manner as in Example 18, except for replacing super absorbent polymer Aquaric CAW-4 of Example 18 with Aronzap RS-2 (aqueous solution polymerization type super absorbent polymer, produced by Toagosei Chemical Industry Co., Ltd.), using the kinds and amounts of the hydrophilic polymer, crosslinking agent and dispersant as shown in Table 3, and adding the hydrophilic polymer at the water content shown in Table 3. The resulting super absorbent polymer was evaluated by the same manner as in Example 1. The results obtained are shown in Table 3.

Example 21

An improved super absorbent polymer was prepared by conducting crosslinking treatment in the same manner as in Example 18, except for replacing super absorbent polymer Aquaric CAW-4 of Example 18 with Aquakeep 10SH-P (suspension polymerization type super absorbent polymer, produced by Sumitomo Seika Chemicals Co., Ltd.), using the kinds and amounts of the hydrophilic polymer, crosslinking agent and dispersant as shown in Table 3, and adding the hydrophilic polymer at the water content shown in Table 3. The resulting super absorbent polymer was evaluated by the same manner as in Example 1. The results obtained are shown in Table 3.

Example 22

In a 1000 ml-volume 4-necked flask equipped with a stirrer, a reflux condenser, and a dropping funnel were charged 125 g of Aquaric CAW-4 having been dried at 120° C. and 0.5 mmHg for 24 hours and 400 ml of cyclohexane, and the mixture was heated to 75° to 80°0 C. After heating, 37.5 g of ion-exchanged water was added thereto, followed by stirring under reflux for 30 minutes thereby to adjust the water content of the super absorbent polymer at 30 parts by weight per 100 parts by weight of the super absorbent polymer. To the thus prepared super absorbent polymer dispersed in cyclohexane was added a previously prepared dispersion of 0.85 g (0.68 wt % based on the super absorbent polymer) of polyethyleneimine (Epomine P-1000, produced by Nippon Shokubai), 2 g of water, 1.0 g of a sugar ester (Ryoto Sugar Ester S-1670, produced by Mitsubishi Kasei Shokuhin K.K.), and 30 ml of cyclohexane, followed by stirring at 75° to 80° C. for 15 minutes. Then, a solution of 0.102 g of polyglycerol polyglycidyl ether (Denacol EX-512, produced by Nagase Kasei) in 4 g of water was added thereto, followed by reacting at 75° to 80° C. for 1 hour to crosslink the polyethyleneimine. The resulting gel was collected and dried under reduced pressure to obtain an improved super absorbent polymer having a crosslinked polyethyleneimine coating layer on the surface thereof. The resulting super absorbent polymer was evaluated by the same manner as in Example 1, and the results obtained are shown in Table 3 below.

Example 23

In a 1000 ml-volume kneader equipped with a spray nozzle were charged 125 g of Aquaric CAW-4 having been dried at 120° C. and 0.5 mmHg for 24 hours and 400 ml of cyclohexane, and the mixture was heated to 75° to 80° C. After heating, 37.5 g of ion-exchanged water was added while stirring, followed by further stirring for 30 minutes to adjust the water content of the super absorbent polymer at 30 parts by weight per 100 parts by weight of the super absorbent polymer. An aqueous solution of 0.25 g (0.2 wt % based on the super absorbent polymer) of polyethyleneimine (Epomine SP-006, produced by Nippon Shokubai) in 5 g of water was added to the water-retained super absorbent polymer through the spray nozzle, followed by stirring at 75° to 80° C. for 15 minutes to form a coating layer of polyethyleneimine on the surface of the super absorbent polymer. Then, an aqueous solution of 0.102 g of polyglycerol polyglycidyl ether (Denacol EX-512, produced by Nagase Kasei) in 4 g of water was added thereto through the spray nozzle, followed by reacting at 75° to 80° C. for 1 hour to crosslink the polyethyleneimine. The resulting gel was dried under reduced pressure to obtain an improved super absorbent polymer having a crosslinked polyethyleneimine coating layer on the surface thereof. The resulting super absorbent polymer was evaluated by the same manner as in Example 1, and the results obtained are shown in Table 3 below.

Example 24

An improved super absorbent polymer was prepared by the same manner as in Example 18, except for replacing Aquaric CAW-4 of Example 18 with Aronzap RS-2, using the kinds and amounts of the hydrophilic polymer, crosslinking agent and dispersant as shown in Table 3, and adding the hydrophilic polymer at the water content shown in Table 3. The resulting super absorbent polymer was evaluated by the same manner as in Example 1. The results obtained are shown in Table 3.

TABLE 3

| Examples | Hydrophilic Polymer Type/MW/wt %*) | Crosslinking Agent Type/wt %*) | Hydrophilic Polymer/ Crosslinking Agent (wt/wt) | Water Content | Dispersant Type/wt %*) | Absorption g/g | Rate of Absorption ml/0.3 g | Rate of Liquid Permeation ml/min | Stability |
|---|---|---|---|---|---|---|---|---|---|
| 18 | PEI/600/0.02 | PGPG/0.01 | 2.0 | 30 | EC/0.5 | 52.7 | 10.5 | 85.5 | Excellent |
| 19 | PEI/70,000/0.68 | PGPG/0.10 | 6.8 | 30 | Not Added | 71.8 | 6.5 | 33.3 | Good |
| 20 | PEI/70,000/0.68 | EGDG/0.10 | 6.8 | 30 | EC/0.5 | 63.4 | 7.9 | 120.7 | Good |
| 21 | PEI/70,000/0.68 | PGPG/0.20 | 3.4 | 30 | EC/0.5 | 62.1 | 18.9 | 98.6 | Good |
| 22 | PEI/70,000/0.68 | PGPG/0.20 | 3.4 | 30 | SuE/0.8 | 53.3 | 13.9 | 86.7 | Excellent |
| 23 | PEI/70,000/0.68 | PGPG/0.20 | 3.4 | 30 | Not Added | 48.8 | 11.1 | 90.0 | Excellent |
| 24 | PEI/70,000/0.68 | PGPG/0.20 | 3.4 | 30 | Not Added | 65.4 | 7.2 | 40.9 | Good |

*)Based on super absorbent polymer

Comparative Examples 1 To 5

A super absorbent polymer was obtained by conducting polymerization by the same manner as in Example 1, except for using the kinds and amounts of the hydrophilic polymer, crosslinking agent and dispersant for reverse phase suspension polymerization shown in Table 4 below and adding the hydrophilic polymer at the water content shown in Table 4. The resulting super absorbent polymer was evaluated by the same manner as in Example 1, and the results obtained are shown in Table 4.

TABLE 4

| Comparative Examples | Hydrophilic Polymer Type/MW/wt %*) | Crosslinking Agent Type/wt %*) | Hydrophilic Polymer/ Crosslinking Agent (wt/wt) | Water Content | Dispersant Type/wt %*) | Absorption g/g | Rate of Absorption ml/0.3 g | Rate of Liquid Permeation ml/min | Stability |
|---|---|---|---|---|---|---|---|---|---|
| 1 | PEI/70,000/0.25 | Not Added | — | 30 | EC/0.5 | 65.3 | 3.1 | 6.7 | Poor |
| 2 | Not Added | PGPG/0.10 | — | 30 | EC/0.5 | 65.2 | 4.8 | 28.9 | Fair |
| 3 | PEI/70,000/2.00 | EGDG/0.05 | 40 | 30 | EC/0.5 | 71.5 | 3.5 | 2.7 | Poor |
| 4 | PEI/70,000/0.005 | PGPG/0.10 | 0.05 | 30 | EC/0.5 | 65.7 | 3.8 | 18.3 | Fair |
| 5 | PEI/70,000/0.25 | PGPG/0.15 | 1.67 | 5 | EC/0.5 | 64.1 | 2.9 | 15.3 | Poor |

*)Based on produced polymer

Example 25

Into a 1000 ml-volume 4-necked flask equipped with a stirrer, a reflux condenser, a dropping funnel, and a tube for introducing nitrogen were charged 400 g of cyclohexane and 0.625 g (0.5 wt % based on the produced polymer) of ethyl cellulose (Ethyl Cellulose N-100, produced by Hercules), and nitrogen gas was blown into the mixture to purge dissolved oxygen. The mixture was heated up to 75° C. Separately, 102.0 g of acrylic acid in a separate flask was diluted with 25.5 g of ion-exchanged water and neutralized by addition of 140 g of a 30 wt % aqueous solution of sodium hydroxide while externally cooling. A solution of 0.204 g of potassium persulfate in 7.5 g of water was added thereto and dissolved, and nitrogen gas was bubbled through the solution to remove any oxygen remaining in the solution. The contents of the flask was added dropwise to the aforementioned 4-necked flask over a period of 1 hour to conduct polymerization. After completion of the polymerization, the reaction mixture was azeotropically dehydrated by means of a drying tube to adjust the water content of the super absorbent polymer to 30 parts by weight per 100 parts by weight of the polymer. To the thus prepared water-retained super absorbent polymer dispersed in the cyclohexene was added a solution of 0.153 g (0.12 wt % based on the produced polymer) of tetraethoxysilane in 5 g of cyclohexane, followed by stirring at 75° to 80° C. for 15 minutes. Then, a solution of 0.077 g (0.061 wt % based on the produced polymer) of polyglycerol polyglycidyl ether (Denacol EX-52, produced by Nagase Kasei) in 4 g of water was added thereto, followed by reacting at 75° to 80° C. for 1 hour to crosslink polyglycerol polyglyciyl ether. The resulting gel was collected and dried under reduced pressure to obtain 126 g of an improved super absorbent polymer. The resulting super absorbent polymer was evaluated by the same manner as in Example 1, and the results obtained are shown in Table 5 below.

Examples 26 To 40

Improved super absorbent polymers were obtained by conducting polymerization and posttreatment by the same manner as in Example 25, except for changing the kinds and amounts of the metallic compound, crosslinking agent, and dispersant for reverse phase suspension polymerization as shown in Table 5, and adding the metallic compound and the crosslinking agent at the water content shown in Table 5. The resulting super absorbent polymers were evaluated by the same manner as in Example 1, and the results obtained are shown in Table 5.

TABLE 5

| Examples | Metallic Compound Type/wt %*) | Crosslinking Agent Type/wt %*) | Water Content | Dispersant Type/wt %*) | Absorption g/g | Rate of Absorption ml/0.3 g | Rate of Liquid Permeation ml/min | Stability |
|---|---|---|---|---|---|---|---|---|
| 25 | LS-2430/0.12 | PGPG/0.061 | 30 | EC/0.5 | 65.3 | 6.5 | 41.2 | Good |
| 26 | LS-1890/0.24 | PGPG/0.061 | 30 | EC/0.5 | 64.6 | 6.3 | 40.3 | Good |
| 27 | PS9125/0.08 | PGPG/0.061 | 30 | EC/0.5 | 64.8 | 6.6 | 44.5 | Excellent |
| 28 | PS9125/0.61 | PVA/0.16 | 30 | SoE/3.0 | 66.1 | 6.7 | 39.9 | Good |
| 29 | PS9125/0.41 | HEC/0.20 | 25 | EC/0.5 | 65.5 | 5.9 | 44.1 | Good |
| 30 | TSL8032/0.16 | PHEA/0.065 | 30 | SoE/3.0 | 59.2 | 5.8 | 28.4 | Good |
| 31 | KBE903/0.12 | EGDG/0.082 | 25 | EC/0.5 | 62.3 | 6.4 | 43.8 | Good |
| 32 | B-1/0.20 | EGDG/0.082 | 30 | SuE/0.5 | 63.6 | 6.8 | 31.0 | Good |
| 33 | B-10/0.12 | SPGE/0.061 | 25 | EC/0.5 | 66.5 | 5.9 | 48.7 | Excellent |
| 34 | T-50/0.08 | PGPG/0.061 | 30 | ES/0.5 | 56.3 | 9.8 | 102.4 | Excellent |
| 35 | T-50/0.24 | HEC/0.12 | 35 | ES/0.5 | 58.1 | 10.1 | 109.8 | Good |
| 36 | T-50/0.20 | PEI/0.20 | 25 | AG/1.0 | 61.4 | 4.9 | 156.7 | Good |
| 37 | TAT/0.12 | GLY/0.082 | 30 | EC/0.5 | 54.4 | 5.9 | 46.2 | Good |
| 38 | TAT/0.12 | DGDG/0.061 | 30 | ES/0.5 | 58.1 | 10.4 | 110.8 | Excellent |
| 40 | IPZ/0.29 | PGPG/0.081 | 30 | EC/0.5 | 56.5 | 5.6 | 58.2 | Good |

*)Based on produced polymer
Note:
1) Metallic Compounds
LS-2430; tetraethoxysilane (produced by Shin-Etsu Chemical Co., Ltd.)
LS-1890; methyltriethoxysilane (produced by Shin-Etsu Chemical Co., Ltd.)

TABLE 5-continued

| Examples | Metallic Compound Type/wt %[*] | Crosslinking Agent Type/wt %[*] | Water Content | Dispersant Type/wt %[*] | Absorption g/g | Rate of Absorption ml/0.3 g | Rate of Liquid Permeation ml/min | Stability |
|---|---|---|---|---|---|---|---|---|

PS1925; polydiethoxysiloxane (produce by Hüls)
TSL8032; dimethylchlorosilane (produced by Toshiba Silicone)
KBE903; 3-aminopropyltriethoxysilane (produced by Shin-Etsu Chemical Co., Ltd.)
B-1; tetrabutoxytitanium (produced by Nippon Soda)
B-10; tetrabutoxytitanium polymer (produced by Nippon Soda)
T-50; diisopropoxybis (acetylacetonate) titanium (produced by Nippon Soda)
TAT; dibutoxybis (triethanolaminato) titanium (produced by Nippon Soda)
IPZ; tetraisopropylzirconate (produced by Dynamite Nobel Japan)
2) Crosslinking Agents
GLY; glycerin (produced by Wako Pure Chemical)
HEC; hydroxyethylcellulose SP400 (produced by Daicel Chemical Industries)
PHEA; polyhydroxyethylacrylate
SPGE; sorbitol polydiglycidylether Denacole EX-611 (produced by Nagase Kasei)
PEI; polyethyleneimine, Epomine SP-200 (MW: 10,000, produced by Nippon Shokubai)

Example 41

Into a 1000 ml-volume 4-necked flask equipped with a stirrer, a reflux condenser and a dropping funnel were charged 125 g of Aquaric CAW-4 (aqueous solution polymerization type super absorbent polymer, produced by Nippon Shokubai) having been dried at 120° C. and 0.5 mmHg for 24 hours, 400 ml of cyclohexane and 0.625 g of ethylcellulose (dispersant: Ethylcellulose N-100, produced by Hercules), and the mixture was heated to 75° to 80° C. After heating, 37.5 g of ion-exchanged water was added thereto, followed by stirring under reflux for 30 minutes thereby to adjust the water content of the super absorbent polymer at 30 parts by weight per 100 parts by weight of the super absorbent polymer. To the thus prepared water-retained super absorbent polymer dispersed in cyclohexane was added a solution of 0.25 g (0.2wt % based on the super absorbent polymer) of tetraethoxysilane (LS-2430, produced by Shin-Etsu Kagaku, K. K.) in 5 g of cyclohexane, followed by stirring at 75° to 80° C. for 15 minutes. Then, a solution of 0.102 g of polyglycerol polyglycidyl ether (Denacol EX-512, produced by Nagase Kasei) in 4 g of water was added thereto, followed by reacting at 75° C. for 1 hour to crosslink the polyglycerol polyglycidyl ether. The resulting gel was collected and dried under reduced pressure to obtain an improved super absorbent polymer. The resulting super absorbent polymer was evaluated by the same manner as in Example 1, and the results obtained are shown in Table 6.

Example 42

An improved super absorbent polymer was obtained by conducting crosslinking treatment in the same manner as in Example 41, except for replacing super absorbent polymer Aquaric CAW-4 of Example 41 with Diawet USII-60 (suspension polymerization type super absorbent polymer, produced by Mitsubishi Petrochemical), using no dispersant and the kinds and amounts of the metallic compound and crosslinking agent as shown in Table 6, and adding the metallic compound and crosslinking agent at the water content shown in Table 6. The resulting super absorbent polymer was evaluated by the same manner as in Example 1, and the results are shown in Table 6.

Example 43

An improved super absorbent polymer was obtained by conducting crosslinking treatment in the same manner as in Example 41, except for replacing Aguaric CAW-4 of Example 41 with Aronzap RS-2 (aqueous solution polymerization type super absorbent polymer, produced by Toa Gosei), using no dispersant and the kinds and amounts of metallic compound and crosslinking agent as shown in Table 6, and adding the metallic compound and crosslinking agent at the water content shown in Table 6. The resulting super absorbent polymer was evaluated by the same manner as in Example 1, and the results obtained are shown in Table 6.

Example 44

An improved super absorbent polymer was obtained by conducting crosslinking treatment in the same manner as in Example 41, except for replacing super absorbent polymer Aquaric CAW-4 of Example 41 with Aquakeep 10SH-P (suspension polymerization type super absorbent polymer, produced by Sumitomo Seika), using the kinds and amounts of the metallic compound and crosslinking agent as shown in Table 6, and adding the metallic compound and crosslinking agent at the amount shown in Table 6. The resulting absorbent polymer was evaluated by the same manner as in Example 1, and the results obtained are shown in Table 6.

Example 45

Into a 1000 ml-volume 4-necked flask equipped with a stirrer, a reflux condenser, and a dropping funnel were charged 125 g of Aquaric CAW-4 (aqueous solution type polymerization super absorbent polymer, produced by Nippon Shokubai) having been dried at 120° C. and 0.5 mmHg for 24 hours and 400 ml of cyclohexane, and the mixture was heated to 75° to 80° C. After heating, 37.5 g of ion-exchanged water was added thereto, followed by stirring under reflux for 30 minutes thereby to adjust the water content of the super absorbent polymer at 35 parts by weight per 100 parts by weight of the super absorbent polymer. To the thus prepared water-retained super absorbent polymer dispersed in cyclohexane was added 0.3 g of an aqueous solution containing 0.125 g (0.10 wt % based on the super absorbent polymer) of methyltriethoxysilane (LS-1890, produced by Shin-Etsu Kagaku, K. K.) having been previously hydrolyzed in an aqueous solution of acetic acid having pH 3.5, followed by stirring at 75° to 80° C. for 15 minutes. Then, a solution of 0.051 g (0.041 wt % based on the super absorbent polymer) of polyglycerol polygycidyl ether (Denacol EX-512, produced by Nagase Kasei) in 4 g of water was added thereto, followed by reacting at 75° to 80° C. for 1 hour to crosslink the polyglycerol polyglycidyl ether. The resulting gel was collected and dried under reduced pressure thereby to obtain an improved super absorbent polymer having a crosslinked layer of polyglycerol polyglycidyl ether on the surface thereof. The resulting super absorbent polymer was evaluated in the same manner as in Example, and the results obtained are shown in Table 6 below.

Example 46

Into a 1000 ml-volume kneader equipped with a spray nozzle were charged 125 g of Aquaric CAW-4 (aqueous solution polymerization type super absorbent polymer, produced by Nippon Shokubai) having been dried at 120° C. and 0.5 mmHg for 24 hours and 400 ml of cyclohexane, and the mixture was heated to 75° to 80° C. After heating, 37.5 g of ion-exchanged was added while stirring, followed by further stirring for 30 minutes to adjust the water content of the super absorbent polymer at 25 parts by weight per 100 parts by weight of the super absorbent polymer. To the water-retained super absorbent polymer was added a solution containing 0.25 g (0.20 wt % based on the super absorbent polymer) of tetraethoxysilane (LS-2430, produced by Toa Gosei), using the kinds and amounts of the metallic compound and crosslinking agent as shown in Table 6, and adding the metallic compound at the water content shown in Table 6. The resulting super absorbent polymer was evaluated by the same manner as in Example 1, and the results obtained are shown in Table 6.

TABLE 6

| Examples | Metallic Compound Type/wt %*) | Crosslinking Agent Type/wt %*) | Water Content | Dispersant Type/wt %*) | Absorption g/g | Rate of Absorption ml/0.3 g | Rate of Liquid Permeation ml/min | Stability |
|---|---|---|---|---|---|---|---|---|
| 41 | LS-2430/0.20 | PGPG/0.082 | 30 | EC/0.5 | 55.1 | 9.6 | 108.3 | Excellent |
| 42 | LS-1890/0.082 | EGDG/0.041 | 35 | Not Added | 54.6 | 8.7 | 110.2 | Good |
| 43 | PS9125/0.12 | PGPG/0.041 | 30 | Not Added | 58.3 | 9.5 | 148.1 | Good |
| 44 | PS9125/0.16 | HEC/0.082 | 30 | SuE/0.5 | 53.2 | 4.9 | 72.9 | Excellent |
| 45 | LS-1890/0.10 | PGPG/0.041 | 35 | Not Added | 56.9 | 9.2 | 102.6 | Excellent |
| 46 | LS-2430/0.20 | PVA/0.082 | 25 | Not Added | 54.4 | 5.9 | 139.2 | Good |
| 47 | TAT/0.24 | PGPG/0.041 | 30 | Not Added | 55.2 | 8.3 | 89.3 | Good |

*)Based on produced polymer duced by Shin-Etsu Kagaku, K. K.) through the spray nozzle, followed by stirring at 75° to 80° C. for 15 minutes. Then, 0.102 g (0.082 wt % based on the super absorbent polymer) of polyvinyl alcohol having a degree of polymerization of 500 (produced by Wako Pure Chemical) in 4 g of water was added thereto through the spray nozzle, followed by reacting at 75° to 80° C. for 1 hour. The resulting gel was dried under reduced pressure to obtain an improved super absorbent polymer. The resulting super absorbent polymer was evaluated by the same manner as in Example 1, and the results obtained are shown in Table 6.

Example 47

An improved super absorbent polymer was obtained by conducting a crosslinking treatment in the same manner as in Example 46, except for replacing super absorbent polymer Aquaric CAW-4 of Example 46 with Anzarop RS-2 (aqueous solution polymerization type super absorbent polymer, produced by Toa Gosei), using the kinds and amounts of the metallic compound and crosslinking agent as shown in Table 6, and adding the metallic compound at the water content shown in Table 6. The resulting super absorbent polymer was evaluated by the same manner as in Example 1, and the results obtained are shown in Table 6.

Comparative Examples 6 To 10

Super absorbent polymers were obtained by conducting polymerization in the same manner as in Example 25 except for using the kinds and amounts of the metallic compound, crosslinking agent, dispersant for reverse phase suspension polymerization as shown in Table 7, and adding the metallic compound and crosslinking agent at the water content shown in Table 7. The resulting super absorbent polymers were evaluated by the same manner as in Example 1, and the results are shown in Table 7.

TABLE 7

| Comparative Examples | Metallic Compound Type/wt %*) | Crosslinking Agent Type/wt %*) | Water Content | Dispersant Type/wt %*) | Absorption g/g | Rate of Absorption ml/0.3 g | Rate of Liquid Permeation ml/min | Stability |
|---|---|---|---|---|---|---|---|---|
| 6 | Not Added | PGPG/0.10 | 30 | Not Added | 54.6 | 8.2 | 110.6 | Fair |
| 7 | LS-2430/0.20 | Not Added | 35 | Not Added | 58.7 | 2.9 | 104.1 | Poor |
| 8 | PS9125/0.15 | PGPG/0.10 | 5 | Not Added | 58.1 | 7.8 | 98.4 | Poor |
| 9 | T-50/0.20 | Nat Added | 30 | Not Added | 59.3 | 3.6 | 72.9 | Poor |
| 10 | T-50/10.0 | PVA/10.0 | 30 | SuE/2.0 | 39.8 | 1.6 | 186.7 | Excellent |

*)Based on produced polymer

Industrial Applicability

According to the present invention, the waterretained super absorbent polymer is added with the polyfunctional compound and the crosslinking agent, followed by heating to form a crosslinked structure comprising the polyfunctional compound and the crosslinking agent. The present invention thus makes it possible for the first time to produce an improved super absorbent polymer having markedly excellent absorption characteristics, such as absorptivity, rate of absorption, liquid permeability, and swollen gel stability with time.

Therefore, taking advantage of its characteristics, the improved super absorbent polymer obtainable by the present invention is useful as a water-absorbing polymer in sanitary napkins, disposable diapers, shirts for adults, tampons, absorbent wadding, and the like.

The gel structure of the improved super absorbent polymer of the present invention hardly undergoes deterioration even when used for an extended period of time and is also rich in elasticity. Therefore, it is useful as a water-retaining material in horticulture or a water-stopping material in civil engineering and is expected to be applicable to cosmetic applicators required to have shape retention, elasticity, water absorbing properties, and air permeability.

We claim:

1. A process for producing an improved super absorbent polymer comprising adding to a water-retained super absorbent polymer retaining 10 to 100 parts by weight of water per 100 parts by weight of the super absorbent polymer, (a) a hydrophilic polymer having two or more reactive groups selected from an amide group, a hydroxyl group, an amino group, an aldehyde group, a sulfo group and a carboxyl group, or a metallic compound of silicon, titanium or zirconium having two or more reactive groups selected from an alkoxyl group, a halogen group, an isocyanate group and an acyloxy group, in an amount of 0.005 to 5 parts by weight per 100 parts by weight of the super absorbent polymer, and (b) a crosslinking agent capable of reacting with the hydrophilic polymer or the metallic compound, provided that;

the crosslinking agent for the hydrophilic polymer is at least one member selected from the group consisting of a polyglycidyl ether, a haloepoxy compound, a polyaldehyde, a polyol and a polyamine, and the crosslinking agent for the metallic compound has two or more functional groups selected from a hydroxyl group, an epoxy group, a carboxyl group, an amino group and a thio group, at a weight ratio of the hydrophilic polymer or the metallic compound to the crosslinking agent of 0.1 to 30; mixing; and allowing the mixture to react by heating.

2. The process according to claim 1, wherein the super absorbent polymer is a hydrophilic polymer having a carboxyl group and/or a carboxylate group.

3. The process according to claim 1, wherein the super absorbent polymer is a hydrophilic polymer obtainable by reverse phase suspension polymerization of an aqueous solution of a hydrophilic monomer having a carboxyl group and/or a carboxylate group, with a water-soluble initiator added thereto.

4. The process according to claim 1, wherein the super absorbent polymer is a polymer or copolymer of acrylic acid or an alkali metal salt of acrylic acid.

5. The process according to claim 1, wherein the hydrophilic polymer is a polyethylene imine.

6. The process according to claim 1, wherein the metallic compound is an alkoxy titanium or an alkoxy silane, and the crosslinking agent for the metallic compound is a polyol and/or a polyglycidyl ether.

7. The process according to claim 4, wherein the polymer of acrylic acid has a degree of neutralization 30 to 90 mol %.

8. The process according to claim 1, wherein the hydrophilic polymer or the metallic compound is added to the super absorbent polymer in an amount of 0.01 to 1 part by weight per 100 parts by weight of the super absorbent polymer.

9. The process according to claim 1, wherein the weight ratio of the hydrophilic polymer or the metallic compound to the crosslinking agent is 0.1 to 20.

10. The process according to claim 1, wherein the water-retained super absorbent polymer retains 20 to 50 parts by weight of water per 100 parts by weight of the super absorbent polymer.

* * * * *